US005584086A

United States Patent [19]
VanWinkle et al.

[11] Patent Number: 5,584,086
[45] Date of Patent: Dec. 17, 1996

[54] THERAPEUTIC PILLOW AND METHOD

[76] Inventors: Tresa A. VanWinkle; Larry K. VanWinkle, both of 1005 Spruce, Alamogordo, N.M. 88310-4919

[21] Appl. No.: 356,448

[22] Filed: Dec. 14, 1994

Related U.S. Application Data

[63] Continuation-in-part of Ser. No. 199,386, Feb. 18, 1994, Pat. No. 5,375,278.

[51] Int. Cl.$^6$ ............................ A47C 20/00; A61F 7/00
[52] U.S. Cl. .................. 5/644; 5/640; 5/490; 607/112; 607/114
[58] Field of Search ............................... 5/480, 462, 448, 5/450, 421, 490, 639, 640, 644, 907, 94; 607/112, 114; 600/15; D6/598, 601

[56] References Cited

U.S. PATENT DOCUMENTS

| | | |
|---|---|---|
| 33,350 | 10/1900 | Gibbs . |
| D. 348,372 | 7/1994 | Keller ........................ D6/598 |
| 2,547,886 | 4/1951 | Poux ............................ 62/1 |
| 2,563,933 | 8/1951 | Hipps et al. ................. 62/91.5 |
| 2,710,008 | 6/1955 | Jensen ......................... 607/114 |
| 3,426,372 | 2/1969 | Enelow ......................... 5/490 |
| 3,943,912 | 3/1976 | Nakayama ................... 600/15 |
| 4,163,297 | 8/1979 | Neumark ..................... 5/446 |
| 4,330,892 | 5/1982 | Fukushima .................. 600/15 |
| 4,381,025 | 4/1983 | Schooley ..................... 607/112 |
| 4,777,346 | 10/1988 | Swanton, Jr. ............... 219/313 |
| 4,805,619 | 2/1989 | Swearingen ................. 607/112 |
| 4,843,662 | 7/1989 | Handelman ................. 5/481 |
| 4,887,326 | 12/1989 | O'Brien et al. .............. 5/490 |
| 4,985,951 | 1/1991 | Lacotte ........................ 5/465 |
| 5,033,137 | 7/1991 | Pedrow ........................ 5/436 |
| 5,138,728 | 8/1992 | Aston ........................... 5/645 |
| 5,163,194 | 11/1992 | Dixon ........................... 5/636 |
| 5,274,865 | 1/1994 | Takehashi ................... 5/421 |
| 5,300,104 | 4/1994 | Gaudreault et al. ........ 607/114 |
| 5,300,105 | 4/1994 | Owens ......................... 607/114 |
| 5,366,491 | 11/1994 | Ingram et al. .............. 607/114 X |
| 5,375,278 | 12/1994 | VanWinkle et al. ........ 5/911 X |
| 5,383,921 | 1/1995 | Barry ........................... 607/114 |

FOREIGN PATENT DOCUMENTS 619610 3/1949 United Kingdom ................ 5/480

OTHER PUBLICATIONS

Advertisement for Comfort Pillow, *Voice of the Mountains*, Vermont Country Store, Winter Catalog (Dec. 1993).
Advertisement for Neck Wrap, *Taylor Gifts* (Jan. 1994).
Advertisement for Elasto-Gel Hot/Cold Therapy Wraps, *Prevention Magazine* (Feb. 1994).
Advertisement for Hot/Cold Beauty Mask, *Beauty Boutique* (Winter 1994).

*Primary Examiner*—Michael F. Trettel
*Attorney, Agent, or Firm*—Dennis F. Armijo

[57] ABSTRACT

Disclosed is a therapeutic pillow. The pillow has a bag-like cover filled with natural granular material having a water content in the range of 5% to 25% by weight. The preferred range of water content is from 9% to 16%. The therapeutic pillow can be in different shapes, such as the shape of a toy for use by children, a pad shape with pockets for inserting hands or feet, or muff-shaped. Also disclosed is a temperature sensor and baffles to keep the filling from gathering. A biomagnetic embodiment is also disclosed.

1 Claim, 2 Drawing Sheets

THERAPEUTIC PILLOW AND METHOD

CROSS-REFERENCE TO RELATED APPLICATIONS

This application is a continuation-in-part application Ser. No. 199,386, filed Feb. 18, 1994, now U.S. Pat. No. 5,375,278, entitled "Therapeutic Pillow and Method" to Tresa VanWinkle, et al., issued on Dec. 27, 1994, the teachings of which are incorporated herein by reference.

BACKGROUND OF THE INVENTION

1. Field of the Invention (Technical Field)

The invention relates to a portable therapeutic pillow which can be either heated or cooled to relieve bodily pain and promote comfort.

2. Background Art

Hot and cold packs have long been used to ameliorate bodily discomfort. The well-known hot water bottle and ice pack have long been in human service: for example, hot water bottles for warming the body and loosening taut muscles; ice packs for reducing swelling and soothing sprains and strains. Variations upon these devices proliferate in the prior art.

U.S. Pat. No. 4,163,297 to Neumark entitled "Mattress", discloses a mattress comprising a plurality of individual pillows for preventing decubitus ulcers (bed sores). The pillows may be filled with grain-like material. There is, however, no disclosure relating to heating, cooling or moisture content of the pillows.

U.S. Pat. No. 4,777,346 to Swanton, Jr., entitled "Electrically Heated Therapeutic Pillow", discloses a liquid or gel-filled pillow. Heating is accomplished by electric current, flow of which is facilitated by compression of conductive foam. U.S. Pat. No. 5,033,137 to Pedrow, entitled "Orthopedic Pillow with Groove for Spine", discloses an orthopedic pillow having a grooved structure for spinal accommodation. A bladder similar to an ice pack or hot water bottle is also provided for warming and cooling. U.S. Pat. No. 5,163,194 to Dixon, entitled "Adjustable Cervical Pillow", discloses a polyurethane foam pillow having a removable, supplemental member which can be a heat pack or a cold pack.

U.S. Pat. No. 4,843,662 to Handelman, entitled "Two Person Seat Case", discloses a stadium seat having straps. U.S. Pat. No. 5,138,728 to Aston, entitled "Interior Container Insert For Any Pillow, Cushion or Stuffed Toy" discloses a removable, washable container adapted to be inserted into any pillow, cushion or stuffed toy to secrete valuables therein. U.S. Pat. No. 4,985,951 to Lacotte et al., entitled "Flexible Mattress Including Vegetable Fibers", discloses a mattress composed, in part, of coconut fibers.

None of the prior art, however, discloses the therapeutic pillow of the subject invention having a natural granular or grain-like filling having a moisture content in the range of 5% to 25% by weight.

SUMMARY OF THE INVENTION (DISCLOSURE OF THE INVENTION)

In accordance with the present invention, there is provided an apparatus and method for applying heat or cold to a body part for ameliorating discomfort. The preferred therapeutic pillow comprises a bag-like covering comprising ears for grasping the therapeutic pillow, the bag-like covering containing a filling comprising natural granular material and the natural granular material comprising a water content having a range of 5% to 25% by weight. An alternative embodiment further comprises a temperature sensor. The bag-like covering can further comprise baffles for containing the natural granular material.

Also disclosed is a temperature transferring therapeutic apparatus comprising a bag-like covering in a shape of a toy, the bag-like covering containing a filling comprising natural granular material and the granular material comprising a water content having a range of 5% to 25% by weight. The preferred toy shape comprises an animal shape. The preferred animal shape comprises a teddy bear shape. The therapeutic apparatus can further comprise a temperature sensor and an outer sleeve. The bag-like covering can further comprise baffles for containing the natural granular material.

Additionally disclosed is a temperature transferring therapeutic apparatus comprising a bag-like covering comprising at least one pocket, the bag-like covering containing a filling comprising natural granular material and the natural granular material comprising a water content of 5% to 25% by weight. The therapeutic apparatus can further comprise a temperature sensor, ears for grasping the therapeutic apparatus and an outer sleeve.

Also disclosed is a biomagnetic therapeutic pillow comprising a bag-like covering, the bag-like covering containing a filling comprising a natural granular material and a magnetic material, and the natural granular material comprising a water content of 5% to 25% by weight. The preferred magnetic material comprises a member selected from the group of metals, polymers, plastics, rubbers and ceramics. The therapeutic apparatus can further comprise a temperature sensor. The bag-like covering can further comprise baffles for containing the natural granular material and ears for grasping the therapeutic pillow.

A temperature transferring, therapeutic apparatus comprising a bag-like covering comprising a muff, the bag-like covering containing a filling comprising natural granular material and the natural granular material comprising a water content of 5% to 25% by weight is also disclosed. The bag-like covering preferably further comprises baffles for containing said natural granular material.

A primary object of the present invention is the provision of a portable therapeutic pillow capable of selectively heating or cooling a variety of body parts.

Another object of the invention is the provision of a therapeutic pillow which is environmentally and anatomically safe.

Still another object of the invention is the provision of a therapeutic pillow that does not require electrical cords or batteries.

Yet another object of the invention is the provision of a therapeutic pillow which is of selected weight, shape, texture and mass to readily conform to selected body parts.

Another object of the present invention is to encourage its use by reluctant children.

Another object is to provide biomagnetic therapy.

A primary advantage of the present invention is its low cost and ease of manufacture.

Another advantage of the invention is its flexibility and ease of application.

Still another advantage of the invention is its construction of naturally occurring materials.

Yet another advantage of the invention is its safety when heating a body part.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

(BEST MODES FOR CARRYING OUT THE INVENTION)

Application of heat and cold have long been recognized as therapeutic for bodily ailments. Localized application of cold, for example, may relieve stress headaches, inflammation and swelling, and the pain of arthritis, minor burns and wounds, and the like. Cold promotes vasoconstriction, thereby preventing swelling while promoting coagulation. Localized application of heat, for example, may promote healing and relieve pain resulting from arthritis, minor wounds, muscle strains, menstrual cramps, and the like. Heat promotes vasodilation, thereby improving blood flow to injured bodily parts.

Figure 1:
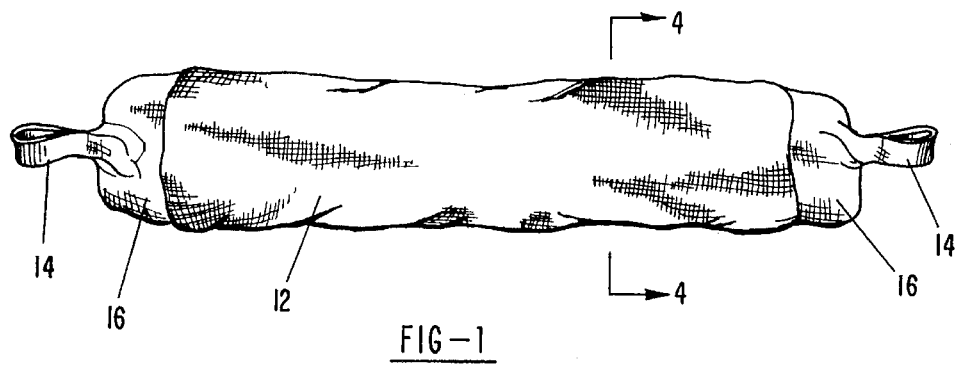
FIG. 1 is a perspective view of an elongated cylindrical embodiment of the invention.
Figure 2:
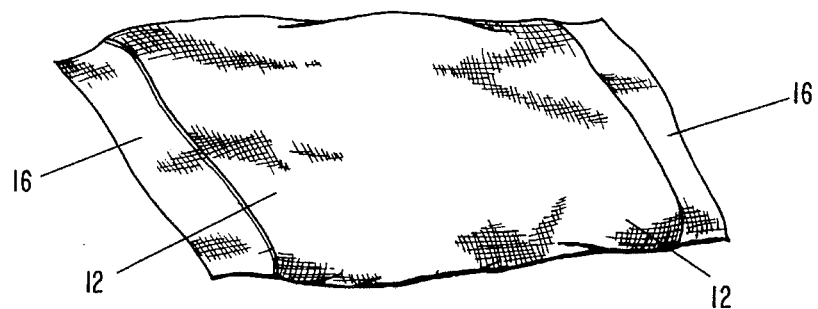
FIG. 2 is a perspective view of an oblong rectangular embodiment of the invention.
Figure 3:
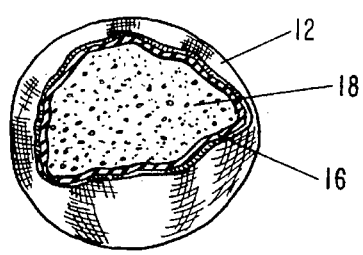
FIG. 3 is a perspective view of a spherical embodiment of the invention.
Figure 4:
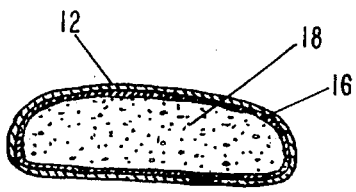
FIG. 4 is a cross-sectional view along A—A' of FIG. 1.

FIGS. 1 and 4 depict the preferred therapeutic pillow 10 of the invention. A tubular outer sleeve 12, preferably of terry cloth, partially surrounds therapeutic pillow 10. Sleeve 12, in addition to protecting and cooling the pillow, is washable. Further, sleeve 12 provides a convenient "tuck" for ears 14, as will be described later. Sleeve 12 may also comprise other natural fibers, for example, wool, cotton, and the like.

Therapeutic pillow 10 further comprises inner bag-like cover 16. Inner cover 16 is also comprised of suitable natural fibers, preferably cotton, or other natural fiber materials. Alternatively, inner cover 16 can comprise any material capable of efficiently transferring heat and containment of filling 18. Inner bag-like cover 16 is partially filled with filling 18.

Sleeve 12 is not necessary for use of the therapeutic pillow 10, therefore inner bag-like covering 16 can be directly applied to the body member. However, washing inner bag-like covering 16 would be difficult when used in this manner and the potential for piercing bag-like cover 16, thus allowing filling 18 to escape, would be enhanced.

Filling 18 comprises naturally occurring grains or granular material. The preferred filling is processed barley, but other natural grains, seeds and natural granular material may be used. The use of such natural materials is important in several respects.

Use of naturally occurring granular and grain-like materials provides "live" weight and mass to the therapeutic pillow. Accordingly, therapeutic pillow 10 can be shaped to conform to any given anatomical area, be it arms, legs, neck, spine, and the like. Further, because of its weight and mass, such conformable shape will tend to be maintained while in position against the body part. Although this specification refers to a tubular form, other forms can be utilized to conform to other body members.

Additionally, and most importantly, use of naturally occurring grain and seeds enables provision of a predetermined range of water content. It is water content which is believed to provide the therapeutic benefit of the therapeutic pillow. A range of 5–25% water content by weight generally provides desired therapeutic results; the preferred range is 9–16% water content by weight. These ranges are considered critical to the efficacy of the therapeutic pillow. Those ordinarily skilled in the art will recognize that other and various materials providing these ranges of water content may be provided as a filler.

Figure 5:
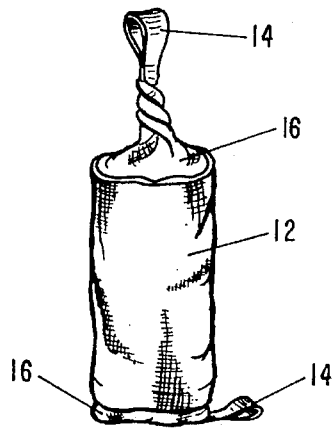
FIGS. 5 and 6 are perspective views of the pillow being prepared for application.
Figure 6:
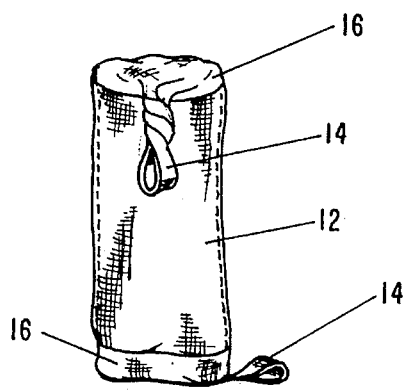

Ears 14 are sewn or otherwise attached to inner cover 16. Ears 14 are used for carrying, positioning, shaping and determining a given consistency for the therapeutic pillow, as shown in FIGS. 5 and 6.

Figure 7:
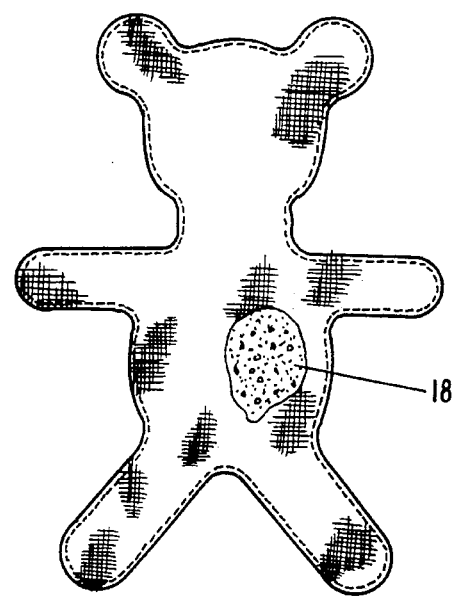
FIG. 7 is a front view of a teddy bear-shaped therapeutic pillow.

The therapeutic pillow can be configured in different shapes, such as toys or animal shapes to encourage its use by reluctant children, or the like. FIG. 7 depicts a typical teddy bear-shaped therapeutic pillow. The teddy bear-shaped therapeutic pillow contains filling 18, similar to the other embodiments. Although only a teddy bear is depicted in FIG. 7, other forms or shapes can be utilized and are made part of this disclosure.

Figure 8:
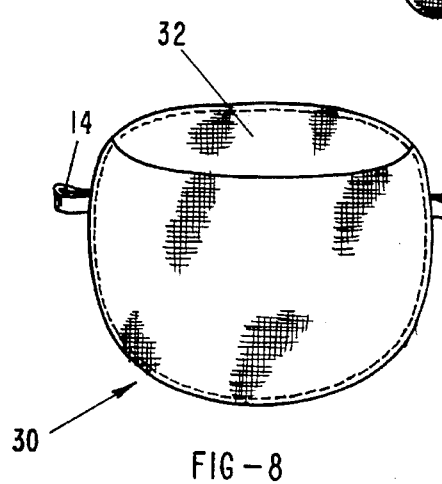
FIG. 8 is a front view of a pad embodiment of a therapeutic pillow.

Another embodiment for the therapeutic pillow is shown in FIG. 8. Although FIG. 8 shows a pancake-shaped pad, other shapes such as square, diamond, rectangular, foot-shaped, hand-shaped, and the like can be used. Pad 30 is primarily used for therapy to hands or feet, but is not limited to these uses. A pad of similar design can be used for sitting upon or to wrap around a body member. Pocket 32 can be added to allow insertion of hands or feet into pad 30. Additional pockets can be located on pad 30 (not shown). Ears 14 for grasping the therapeutic pillow can be utilized in this embodiment also.

Figure 9:
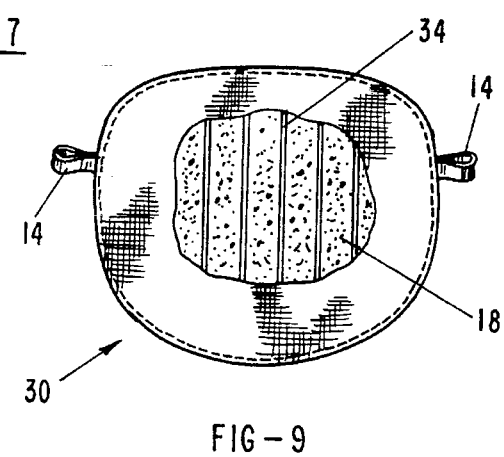
FIG. 9 is a cut out view of FIG. 8 showing baffles.

To keep filling 18 from gathering in one area of pad 30, baffles 34 can be added as depicted in FIG. 9. By utilizing baffles 34, heat or cold can be uniformly distributed, no matter in what orientation the therapeutic pillow is. Baffles 34 can be sewn in pad 30, as shown, or other well-known methods, such as glue or preformed baffles, could be used (not shown). Baffles 34 can be incorporated in any of the embodiments of the therapeutic pillow and this disclosure is not meant to limit the use of baffles to the embodiment of FIG. 9.

Figure 10:
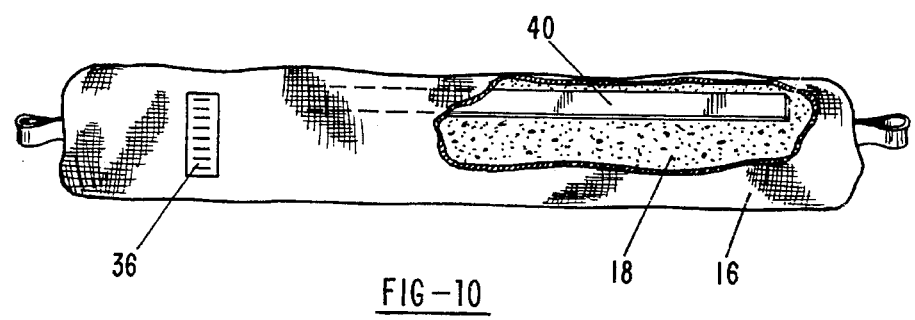
FIG. 10 is a front view of a biomagnetic therapeutic pillow.

To avoid overexposure to heat or cold transferred from the therapeutic pillow to the body member, or to determine when the temperature transfer properties of the pillow are exhausted, temperature sensor 36 can be affixed to the therapeutic pillow as shown in FIG. 10. Temperature sensor 36 is mounted to the therapeutic pillow for easy viewing by the user. Temperature sensor 36 can be of several known varieties, such as a thermometer that registers the temperature, or a material that changes colors as the temperature changes. These types of apparatuses are well-known in the art. Although the temperature sensor 36 is shown only in the embodiment of FIG. 10, it can be utilized with all of the embodiments of the therapeutic pillow.

In addition to thermal transfer, biomagnetic therapy can be accomplished by adding a material within the therapeutic pillow that receives and holds a magnetic charge. FIG. 10 depicts a biomagnetic therapeutic pillow. Magnetic material 40 is disposed within the therapeutic pillow as shown. Magnetic material 40 can be one or more bars affixed within inner bag 16. Magnetic bar 40 can be held in place by affixing it to inner bag 16 by sewing it to inner bag 16, sewing a pocket to inner bag 16 (not shown), or by using adhesives or any other affixing method well-known in the art. In addition to magnetic bars, magnetic material 40 can be granules in similar sizes of filler 18 and mixed in with filler 18. This disclosure is not limited to the embodiments as described above, but includes any configuration of magnetic materials contained within a therapeutic pillow. Magnetic material 40 can comprise metals, polymers, plastics, rubbers, ceramics or any other material capable of receiving and holding a magnetic charge. Magnetic material 40 can be utilized in any of the embodiments of the therapeutic pillow.

Figure 11:
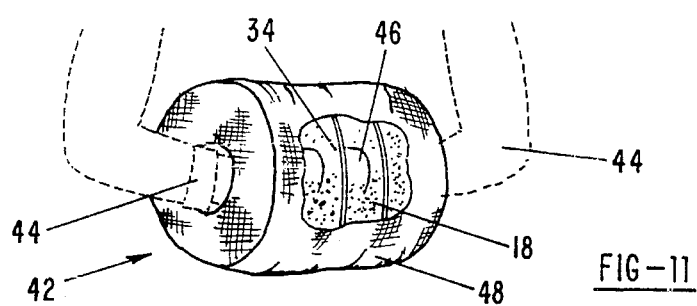
FIG. 11 is a perspective view of a muff therapeutic pillow.

FIG. 11 shows the muff embodiment of the therapeutic pillow. Muff 42 is a tubular covering for hands 44, or the like, which contains the natural granular material 18 sandwiched between inner tubular covering 46 and outer tubular covering 48. Although FIG. 11 shows only hands inside muff 42, any body extremity can be placed inside for heating or cooling. Baffles 34, a temperature sensor and magnetic material can be incorporated in this embodiment also (not shown). This embodiment of the invention is especially effective for preventing swelling, by providing cooling to an injured extremity such as a hand or arm after an injury. It also provides effective relief for arthritis sufferers and can be used to warm cold hands or feet.

Industrial Applicability

The invention is further illustrated by the following non-limiting examples.

EXAMPLE I

Assuming that it is desired to cool the affected body part, the therapeutic pillow is placed in a freezer at least 30 minutes prior to use. The therapeutic pillow may first be sealed in a plastic bag to prevent freezer odor from being absorbed by the pillow. When applying the pillow, the desired consistency and firmness are first determined. The pillow is held up by one ear, allowing the filler contents to settle to the desired firmness. The ear and attached inner cover are then twisted and tucked into the outer sleeve, as shown in FIGS. 5 and 6. The therapeutic pillow is then directly applied to the affected body part. For example, to relieve a stress-related headache, the cooled therapeutic pillow is wrapped about the neck while the subject is in a supine or sitting position.

EXAMPLE II

If it is desired to heat an affected body part, the therapeutic pillow may be warmed, for example, in a microwave oven. Depending upon its size, the pillow is heated no longer than 5 minutes (overheating is to be avoided) and may be reheated hourly. Again, as with cooling, and as depicted in FIGS. 5 and 6, the desired firmness is determined and the pillow is applied to the affected body part.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. A therapeutic pillow comprising:
   a substantially tubular shaped bag-like covering comprising ears for grasping said therapeutic pillow wherein said ears for grasping comprise a first ear affixed to a first end and a second ear affixed to a second end of said substantially tubular shaped bag-like covering;
   said substantially tubular shaped bag-like covering containing a filling comprising natural materials; and
   said natural materials comprising a water content having a range of 5% to 25% by weight.

* * * * *

US005584086B1

REEXAMINATION CERTIFICATE (4220th)

United States Patent [19]
VanWinkle et al.

[11] B1 5,584,086
[45] Certificate Issued Nov. 28, 2000

[54] THERAPEUTIC PILLOW AND METHOD

[75] Inventors: Tresa A. VanWinkle; Larry K. VanWinkle, both of 1005 Spruce, Alamogordo, N. Mex. 88310-4919

[73] Assignees: Tresa A. VanWinkle; Larry K. VanWinkle, both of Alamogordo, N. Mex.

Reexamination Request:
No. 90/005,287, Mar. 8, 1999

Reexamination Certificate for:
Patent No.: 5,584,086
Issued: Dec. 17, 1996
Appl. No.: 08/356,448
Filed: Dec. 14, 1994

Related U.S. Application Data

[63] Continuation-in-part of application No. 08/199,386, Feb. 18, 1994, Pat. No. 5,375,278.
[51] Int. Cl.[7] .............................. A47C 20/00; A61F 7/00
[52] U.S. Cl. ......................... 5/644; 5/640; 5/490; 5/636; 5/906; 5/658; 607/112; 607/114
[58] Field of Search ............................... 5/480, 462, 448, 5/450, 421, 490, 639, 640, 644, 907, 94; 607/112, 114; 608/5; D6/598, 601

[56] References Cited

U.S. PATENT DOCUMENTS

| | | |
|---|---|---|
| 3,889,684 | 6/1975 | Lebold . |
| 4,232,663 | 11/1980 | Newton . |
| 4,243,041 | 1/1981 | Paul . |
| 4,347,848 | 9/1982 | Hubbard et al. . |
| 4,576,169 | 3/1986 | Williams . |
| 4,676,247 | 6/1987 | Van Cleve . |
| 4,754,511 | 7/1988 | Sargent . |
| 4,945,589 | 8/1990 | Carey . |
| 5,029,577 | 7/1991 | Sarkozi . |
| 5,056,508 | 10/1991 | Brunnell . |
| 5,179,942 | 1/1993 | Drulias et al. . |
| 5,295,949 | 3/1994 | Hathaway . |
| 5,300,104 | 4/1994 | Gaudreault et al. . |
| 5,363,524 | 11/1994 | Lang . |

*Primary Examiner*—Michael Trettel

[57] ABSTRACT

Disclosed is a therapeutic pillow. The pillow has a bag-like cover filled with natural granular material having a water content in the range of 5% to 25% by weight. The preferred range of water content is from 9% to 16%. The therapeutic pillow can be in different shapes, such as the shape of a toy for use by children, a pad shape with pockets for inserting hands or feet, or muff-shaped. Also disclosed is a temperature sensor and baffles to keep the filling from gathering. A biomagnetic embodiment is also disclosed.

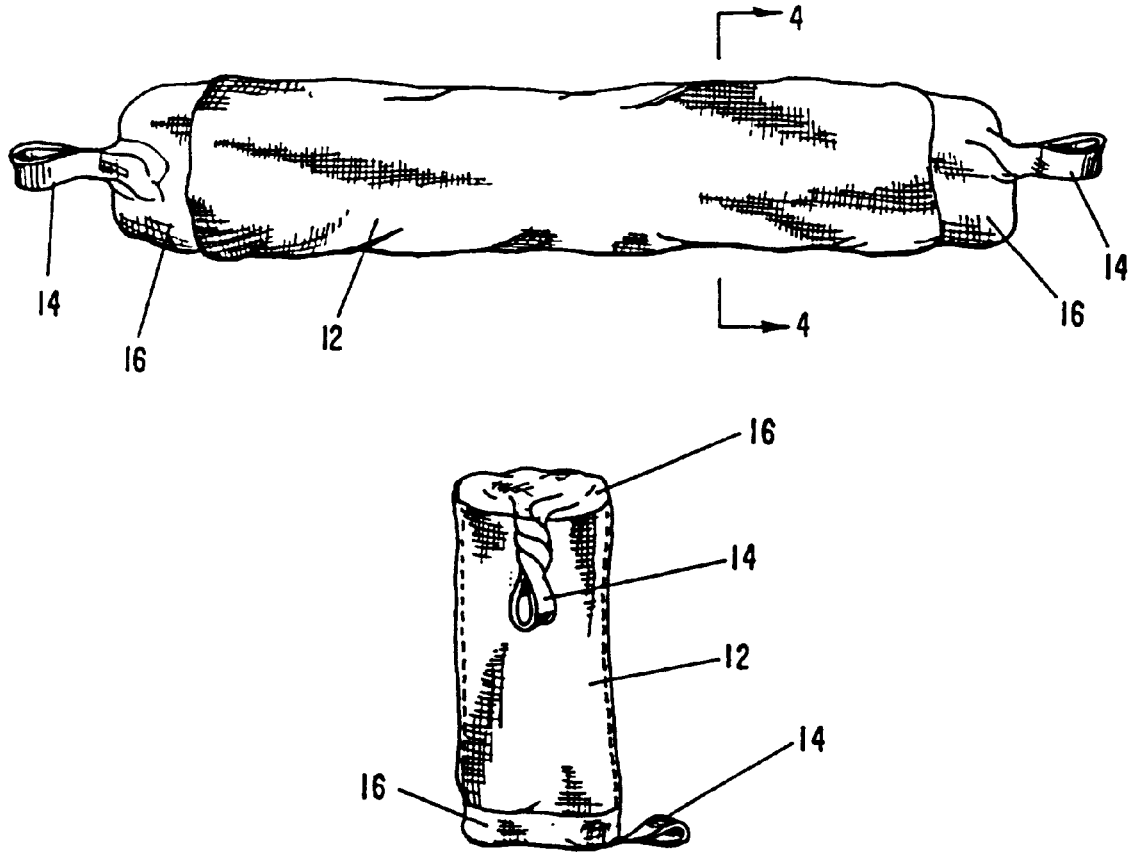

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

1. A therapeutic pillow comprising:

a substantially tubular shaped bag-like covering comprising ears for grasping said therapeutic pillow wherein said ears for grasping comprise a first ear affixed to first end and a second ear affixed to a second end of said substantially tubular shaped bag-like covering;

said substantially tubular shaped bag-like covering *comprising a closed bag-like covering*, containing a filling comprising natural materials, *said filling directly contacting and partially filling said bag like covering*; and said natural materials comprising a water content having a range of 5% to 25% by weight.

* * * * *